(12) United States Patent
Davis

(10) Patent No.: US 6,176,824 B1
(45) Date of Patent: *Jan. 23, 2001

(54) FIBEROPTICALLY ILLUMINATED APPLIANCES

(76) Inventor: James M. Davis, 4687 Pond Apple Dr. South, Naples, FL (US) 33999

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/838,822

(22) Filed: Apr. 10, 1997

Related U.S. Application Data (60) Provisional application No. 60/029,664, filed on Oct. 29, 1996, and provisional application No. 60/035,518, filed on Jan. 15, 1997.

(51) Int. Cl.$^7$ ....................... A61B 1/06
(52) U.S. Cl. .............. 600/178; 600/191; 600/212; 600/241; 600/223
(58) Field of Search .................. 600/121, 160, 600/177, 178, 182, 191, 199, 212, 241; 433/29, 31; 362/804, 32

(56) References Cited

U.S. PATENT DOCUMENTS

| | | |
|---|---|---|
| 849,209 | 4/1907 | Crawford . |
| 1,542,183 | 6/1925 | Steinberg ............................ 433/29 |
| 2,161,151 | 6/1939 | Freedman . |
| 2,247,258 | 6/1941 | Shepard . |
| 3,086,289 | 4/1963 | Orsing . |
| 3,349,764 | 10/1967 | Edinger, et al. . |
| 3,397,687 | 8/1968 | Kirchdoerfer . |
| 3,541,583 | 11/1970 | Deuschle . |
| 3,683,503 * | 8/1972 | Klein ....................... 433/29 |
| 3,716,047 | 2/1973 | Moore . |
| 3,774,614 | 11/1973 | Cook . |
| 3,848,587 | 11/1974 | McDonald . |
| 3,851,642 | 12/1974 | McDonald ............... 600/212 |
| 3,994,287 * | 11/1976 | Turp et al. .................. 604/169 |
| 4,020,556 * | 5/1977 | Sotman .................... 433/29 |
| 4,037,588 | 7/1977 | Heckele . |
| 4,204,328 | 5/1980 | Kutner . |
| 4,306,546 | 12/1981 | Heine et al. ............... 600/182 |
| 4,344,419 | 8/1982 | Burgin .................. 600/212 |
| 4,403,956 * | 9/1983 | Nakanishi ................ 433/29 |
| 4,562,832 | 1/1986 | Wilder, et al. . |
| 4,567,882 * | 2/1986 | Heller ..................... 600/120 |
| 4,597,030 | 6/1986 | Brody, et al. . |
| 4,605,990 | 8/1986 | Wilder, et al. . |
| 4,629,425 * | 12/1986 | Detsch ..................... 433/31 |
| 4,671,283 * | 6/1987 | Hoskin et al. ............. 606/211 |
| 4,697,578 | 10/1987 | Burgin ................... 600/212 |

(List continued on next page.)

| | | |
|---|---|---|
| 4,807,599 | 2/1989 | Robinson, et al. . |

FOREIGN PATENT DOCUMENTS

| | | | |
|---|---|---|---|
| 3939-859 | 6/1991 | (DE) . | |
| 158149 | 2/1921 | (GB) | ................. 600/160 |

* cited by examiner

Primary Examiner—John P. Leubecker
(74) Attorney, Agent, or Firm—William E. Noonan (57) ABSTRACT

A fiberoptically illuminated appliance is disclosed. The appliance includes a light source and an elongate fiberoptic cable, which is operably engaged to the light source and which conducts light from the light source therethrough. A translucent appliance is operated in a conventional manner to perform a primary predetermined function, which function is exclusive of lighting. The appliance includes a continuous light conducting pathway that is uninterrupted by air and a light-emitting surface formed on the periphery of the appliance and communicably connected to the light-conducting pathway. The cable and the appliance are communicably interengaged. Light is directed from the cable through the continuous light-conducting pathway to the light-emitting surface, from which surface light is projected to illuminate the primary predetermined function.

3 Claims, 6 Drawing Sheets

U.S. PATENT DOCUMENTS

| | | | |
|---|---|---|---|
| 4,819,620 | 4/1989 | Okutsu | 600/114 |
| 4,872,837 | 10/1989 | Issalene, et al. . | |
| 4,909,506 | 5/1978 | Pilgrim . | |
| 4,979,498 | 12/1990 | Oneda et al. | 600/123 |
| 4,992,047 | 2/1991 | Warner . | |
| 4,996,976 | 3/1991 | Nakagawa . | |
| 5,030,090 | 7/1991 | Maeda et al. | 433/29 |
| 5,078,603 * | 1/1992 | Cohen | 433/91 |
| 5,156,604 | 10/1992 | Hessel . | |
| 5,165,387 * | 11/1992 | Woodson | 600/114 |
| 5,178,536 * | 1/1993 | Werly | 433/29 |
| 5,203,696 * | 4/1993 | Gonser | 433/29 |
| 5,281,134 * | 1/1994 | Schultz | 433/29 |
| 5,306,143 | 4/1994 | Levy | 433/29 |
| 5,318,009 | 6/1994 | Robinson . | |
| 5,394,863 | 3/1995 | Sanford et al. | 600/199 |
| 5,476,379 * | 12/1995 | Disel | 433/29 |
| 5,587,284 | 12/1996 | Brattesani | 433/29 |
| 5,588,950 * | 12/1996 | Sano et al. | 600/178 |
| 5,609,562 * | 3/1997 | Kaalt | 600/114 |
| 5,685,820 * | 11/1997 | Riek et al. | 600/114 |
| 5,733,241 * | 3/1998 | King | 600/114 |
| 5,797,944 * | 8/1998 | Nobles et al. | 600/101 |

FIBEROPTICALLY ILLUMINATED APPLIANCES

RELATED APPLICATIONS

This application is a continuation-in-part of U.S. Provisional patent application Ser. No. 60/029,664, filed Oct. 29, 1996, and Ser. No. 60/035,518 filed Jan. 15, 1997.

FIELD OF THE INVENTION

This invention relates to fiberoptically illuminated appliances and, more particularly, to medical, industrial and consumer products, which employ a translucent body for transmitting and projecting fiberoptic illumination.

BACKGROUND OF THE INVENTION

Many products perform functions that require illumination. In particular, the medical and dental areas include numerous procedures where optimal lighting conditions are necessary. When performing an operation, a surgeon almost always requires precisely directed lighting to obtain a clear view of the anatomical region being operated upon. Diagnostic procedures within the gastrointestinal tract typically require a fiberoptically illuminated scope. Dentists too utilize headlamps and other types of overhead lighting to obtain an improved view within a patient's mouth. Such lighting requirements are described in my co-pending patent application Ser. No. 60/029,664 filed Oct. 29, 1996.

To date, medical and dental appliances have been lighted primarily through the use of fiberoptic illuminators which project light through an attached cable containing glass or plastic fibers. The cable is typically connected to a surgical instrument or headlight device that projects light onto the area to be illuminated. Certain of the surgical instruments and appliances used for these procedures are manufactured with a dedicated channel containing glass or plastic fiber, which conveys light to the point where it is finally projected on the operative sight. See, for example, Schultz, U.S. Pat. No. 5,281,134, which is directed to a dental instrument and Moore et al., U.S. Pat. No. 3,716,047, which relates to a disposable light conductive speculum. The latter patent employs a dedicated light bar that is mounted to a speculum. Light is projected from a distal end of the bar, through the air and toward the area of the body cavity being examined.

Unfortunately, most of the previously known medical and dental appliances are not optimally illuminated. The need to project light through glass or plastic fiber contained in a dedicated channel causes the amount of light to be restricted and typically creates a small spot of light rather than broadcasting light over a wider area. Standard headlamps and hand-held lights are simply impractical and inadequate for examining region's inside a patient's mouth, nose, ears, throat, rectum and genital tract. Obviously, such devices are useless for examinations of the gastrointestinal tract. Not only are conventional medical and dental instruments inadequately illuminated, they are usually relatively complicated and expensive to manufacture and maintain. And most are not readily disposable. As a result, inconvenient and often expensive sterilization processes and equipment are required in order to reuse these instruments.

SUMMARY OF THE INVENTION

It is therefore an object of the present invention to provide an improved fiberoptically illuminated appliance that employs the standard operational portion of the appliance to conduct and emit light.

It is a further object of this invention to provide a fiberoptically illuminated appliance that achieves significantly improved lighting in a wide variety of medical, industrial and consumer product applications.

It is a further object of this invention to provide a fiberoptically illuminated appliance that is disposable and which may be mass produced quickly, conveniently and inexpensively.

It is a further object of this invention to provide a fiberoptically illuminated appliance that may be used with a wide variety of conventional fiberoptic illuminators.

It is a further object of this invention to provide a fiberoptically illuminated appliance that provides for significantly improved illumination of various openings and areas within the human body.

It is a further object of this invention to provide a fiberoptically illuminated appliance that does not require a dedicated light channel in order to transmit light.

This invention results from a realization that the body of an operational appliance may be used to conduct light and illuminate the operation being performed. This is accomplished by constructing the appliance of a light weight translucent material that transmits and projects fiberoptic illumination toward the function being lighted. By employing the appliance itself as a light projector, significantly improved lighting is achieved in a wide variety of medical, industrial and consumer applications.

This invention features a fiberoptically illuminated appliance that includes a light source and an elongate fiberoptic cable, which is operably interengaged to the light source and which conducts light from the light source therethrough. There is an appliance, which includes translucent operational means that are operated in a conventional manner for performing a primary predetermined function, which function is exclusive of lighting. The operational means define a continuous, light-conducting pathway, uninterrupted by air and include a light-emitting surface formed on the periphery of the operational means and communicably connected to the light-conducting pathway. There are means for communicably interengaging the cable and the operational means and directing light from the cable through the continuous light-conducting pathway to the light-emitting surface, from which surface light is projected to illuminate the primary predetermined function.

In a preferred embodiment, the appliance is a medical appliance, which may be introduced into and engaged with the human body. The translucent operational means may include a solid, light-conducting plastic. The appliance may consist exclusively of such a plastic. The light-emitting surface may cover a majority of the translucent operational means. The light-emitting surface may cover a majority of the light conductive plastic such that light transmitted to the appliance is emitted from a majority of the peripheral surface of the appliance. The continuous, light-conducting pathway may form a majority of the operational means.

The invention also discloses a method of illuminating a primary predetermined function, which function is exclusive of lighting, utilizing an appliance as described above.

BRIEF DESCRIPTION OF THE DRAWINGS

Other objects, features and advantages will occur from the following description of preferred embodiments and the accompanying drawings, in which.

DETAILED DESCRIPTION OF PREFERRED EMBODIMENTS

Figure 1:
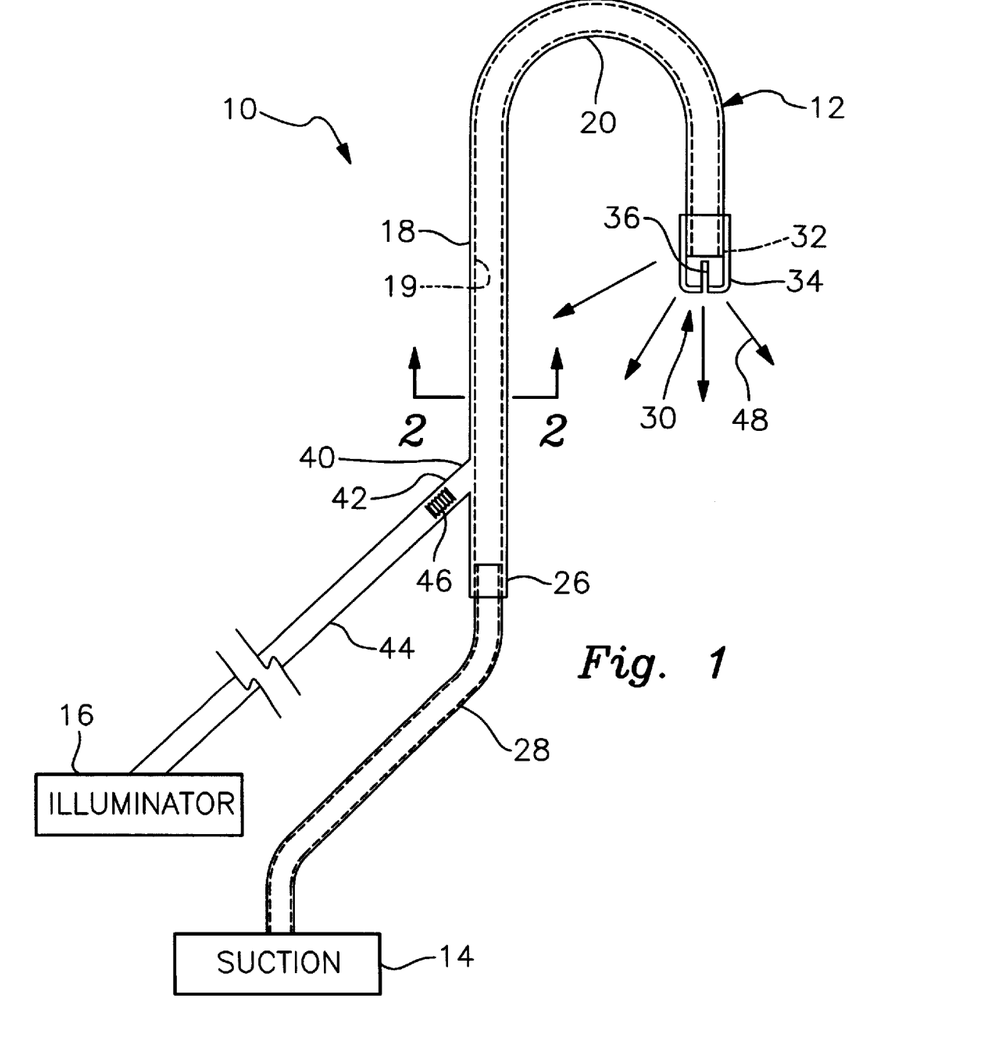
FIG. 1 is an elevational, partly schematic view of an illuminated dental suction appliance constructed according to this invention.
Figure 2:
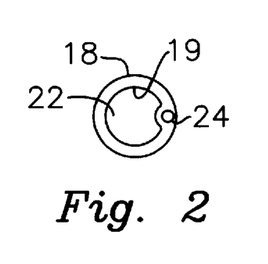
FIG. 2 is a cross sectional view taken along line 2—2 of FIG. 1.

There is shown in FIG. 1 a dental suction appliance 10 that is used to illuminate the interior of a dental patient's mouth so that appropriate dental work may be performed. Appliance 10 includes a disposable suction component 12 that is releasably interconnected to both a conventional suction source 14 and an illuminator device 16. Suction source 14 comprises a standard dental suction apparatus that will be known and understood to persons skilled in the art. Illuminator 16 comprises a standard fiberoptic illuminator having a halogen, xenon or other known type of light source. Suction component 12 includes an elongate tubular member 18 composed of a preferably translucent or other light-conducting plastic material. Tubular member 18 is light-weight and flexible. The tubular member is curved to include a hook portion 20. As shown in FIG. 2, member 18 has a tubular wall 19 and a central bore 22. Wall 19 carries an elongate, bendable shaping element 24 comprising wire or similar material. Element 24 should be flexible and able to maintain the condition into which it is flexed. This permits tubular member 18 to be formed into the curved or hooked shape shown in each of the embodiments herein. See, in particular, hooked portion 21 in FIG. 1. The material comprising the elongate element should be appropriate for use in a dental patient's mouth.

Figure 3:
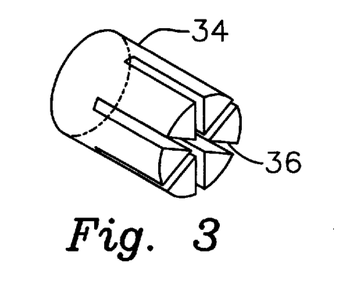
FIG. 3 is a perspective view of a preferred light projection tip component of the suction device.

A first, lower end 26 of tubular member 18 has an opening that receives one end of a suction conduit 28. The other end of suction conduit 28 is communicably and operably interconnected to suction source 14. Proximate the opposite, upper end of tubular member 18, the suction component 12 includes an inlet 30. More particularly, end 32 of tubular member 18 carries an enlarged or bulbous tip 34, which is shown alone in FIG. 3. Tip 34 comprises a translucent material and has a light projecting peripheral surface. This material should likewise be suitable for insertion into a dental patient's mouth. The tip includes a plurality of slots 36 that are formed radially in the distal end of tip 34 and extend longitudinally for at least a portion of the length of the tip. As best shown in FIG. 1, tip 34 includes an interior cavity that receives the open upper end 32 of tubular member 34. As a result, the slotted tip 34 and the open upper end 32 of tubular member 18 define an inlet 30 through which saliva, blood and water are sucked into appliance 10. Hook 20 is engaged with a patient's lip and tip 34 is introduced into the patient's mouth. Suction 14 is operated so that liquids are drawn from the mouth through slots 36 into tubular member 18 and, from there, into a conventional disposal system or container. This portion of the apparatus and its function are known and essentially exhibited by previous dental suction appliances.

The performance of the dental suction appliance is improved considerably by the incorporation of illumination into the appliance. In particular, illuminator 16 is operably interconnected to suction component 12 in the following manner. The suction component 12 includes a "Y" junction 40 proximate the lower end of tubular member 18. The "Y" junction includes a branch element 42 that is unitarily interconnected to and branches off from tubular member 18. Branch 42 comprises the same material which forms the tubular member and is typically unitarily formed with the tubular member in a molding process. The branch element includes a transparent or other light-conducting material. A light-conducting tube or fiber 44 is releasably engaged with branch 42 by means of complementary threads 46 or some other type of coupling structure. The opposite end of fiber 44 is optically engaged with illuminator 16. As a result, fiber 44 conducts light from illuminator 16 to branch 42 and thereby to suction component 12. The end of fiber 44 that is attached to branch 42 comprises a light outlet, which projects light in a narrow beam into branch 42. The branch conducts this light to the light transmitting wall 19 of tubular member 18. As a result, light is transmitted along the length of member 18 to upper end 32 and light projecting tip 34, which are located in the patient's mouth. Light is projected, in the manner indicated by arrows 48 from tip 34 so that the interior of the patient's mouth is brightly illuminated. The dentist can then readily perform necessary dental work. The light is projected from an appliance directly within the patient's mouth. Constant adjustment of a remote dental lamp and the annoying interruptions that typically accompany this procedure are therefore avoided.

To effectively transmit the light from fiber 44 to tip 34, suction component 12 should be composed of a material that effectively conducts the light along the length of tube 18, but does this with a minimum of radial light loss. To accomplish this, a transparent material may be employed. A coating may be applied on the outer surface of the transparent or otherwise translucent material to minimize diffusion and dispersion of the light. Alternatively, a transparent, light-conducting material that inherently exhibits minimal radial light dispersion may be used.

A particularly beneficial feature of this invention is the disposability of suction component 12. The flexed tubular member and unitary branch element are mass produced through a molding process which minimizes the manufacturing time and expense. Likewise, the tip is preferably molded. In alternative embodiments, the tip may be formed unitarily with the tubular member. Various sizes and shapes of tips may be utilized. A generally cylindrical shape is shown in FIG. 1. However, in alternative embodiments, a more bulbous shape may be utilized. After each use, suction component 12 may be readily detached, disposed of and replaced with a new suction component. Replacement is performed simply by detaching fiber 44 from branch 42 and removing end 26 of tubular member 18 from suction conduit 28. A new suction component 12 is then installed by reengaging fiber 44 and suction conduit 28 with the branch 42 and tubular member 18, respectively, of the new suction component. Although disposability is preferred, in certain embodiments, a more permanent suction component, which is sterilized between patients, may be utilized. In still other embodiments, simply the light projecting tip 34 may be replaced.

Figure 4:
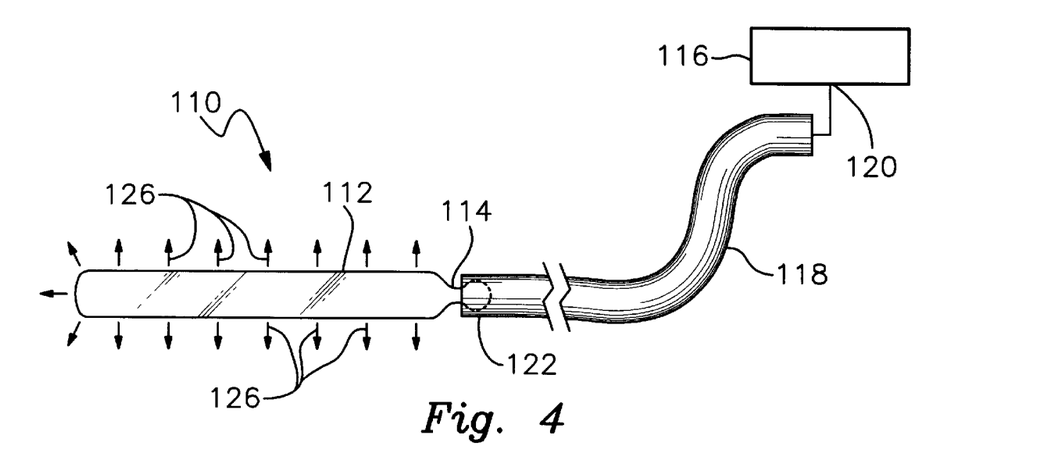
FIG. 4 is a partly schematic, plan view of an illuminated tongue depressor, manufactured according to this invention.
Figure 5:
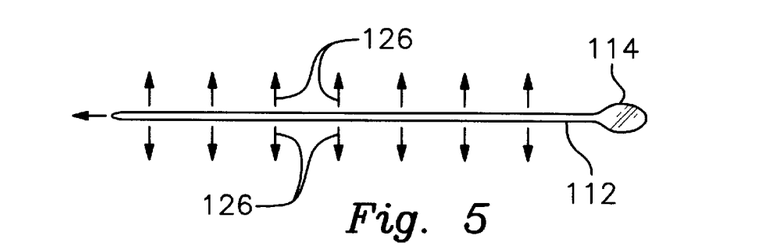
FIG. 5 is an elevational view of the tongue depressor of FIG. 4.

There is shown in FIG. 4 a fiberoptically illuminated tongue depressor appliance 110 that is used to illuminate the interior of a patient's mouth during an examination of the throat and oral cavity. Appliance 110 includes a disposable tongue depressor 112. The tongue depressor comprises an elongate piece of transparent, light-conducting plastic material. As shown in FIG. 5, depressor 112 is substantially flat. A rounded or bulbous element 114 is formed at one end and defines a light inlet for the tongue depressor. Depressor 112 should include a lightweight and inexpensive flexible material and should be capable of being operated in a conventional manner to hold a patient's tongue in place. The plastic material comprising the tongue depressor should be appropriate for use in the patient's mouth.

The tongue depressor is releasably interconnected to a conventional fiberoptic illuminator device 116. The illuminator comprises a standard fiberoptic illuminator commonly used in medical procedures and having a halogen, neon or other known type of light source. Illuminator 116 is operably interconnected to depressor 112 by a light-conducting tube or fiber 118. The optical fiber includes a first end 120 that is interengaged with illuminator 116 by means of a plug or other known fiberoptic connecting component. The opposite end 122 of fiber 118 receives and operably interengages bulbous inlet 114 of tongue depressor 112. Fiber end 122 defines a light outlet which transmits light from fiber 118 to inlet 114 of depressor 112.

In operation, illuminator 116 is activated so that light is transmitted through fiber 118. This light is then transmitted through inlet 114 into tongue depressor 112. The entire outer surface of the tongue depressor comprises a light projecting material. As a result, light is emitted from the depressor as indicated by arrows 126 in FIGS. 4 and 5. In certain embodiments, the outer surface of the depressor may be frosted to reduce the glare of emitted light 126.

The physician introduces tongue depressor 112 into the patient's mouth, engages the tongue and holds it down in a standard manner. At the same time, light is projected from the depressor into the interior of the patient's mouth and the oral cavity is brightly illuminated. The physician can then fully and properly examine the mouth and throat. He or she is not required to hold an examination light in the other hand. Overhead lighting adjustments are eliminated, as are fiberoptic headlamps. The annoying interruptions, distractions and restrictions that these implements normally introduce into the procedure are thereby eliminated.

To effectively transmit the light from fiber 118 through tongue depressor 112, the tongue depressor should be composed of a material that effectively conducts light along the entire length of the depressor and at the same time permits light to be dispersed laterally from the peripheral surface of the depressor. Various light conductive materials may be utilized for this purpose.

A particular beneficial feature of this invention is the disposability of tongue depressor 112. The depressor is mass produced through a conventional molding process, which minimizes the manufacturing time and expense. A flexible, light-conducting plastic should be employed. Various sizes and shapes of depressors may be utilized and particular dimensions are not a limitation of this invention. However, typically, the tongue depressor will be generally elongate and flat, as shown in the drawings. After each use, the tongue depressor is quickly and easily detached from fiber 118, disposed of and replaced with a new tongue depressor, which is fitted into the open end 122 of tubular fiber 118. Although disposability is preferred, in certain embodiments, a more permanent tongue depressor, which is sterilized between patients, may be utilized.

Figure 6:
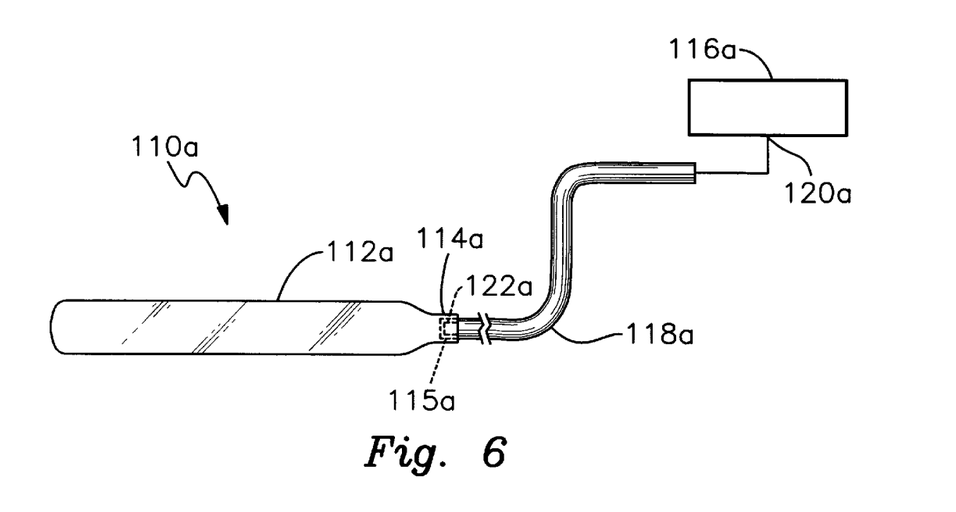
FIG. 6 is a partly schematic, plan view of an illuminated tongue depressor that utilizes a different type of fitting.

An alternative illuminated tongue depressor's appliance 110a is illustrated in FIG. 6. Appliance 110a includes an elongate, flexible tongue depressor 112a. The tongue depressor again comprises a transparent, light-conducting and light projecting material. The primary difference between depressor 112a and the previously described tongue depressor is the use of a female inlet 114a. This inlet includes a slot or receptacle 115a that receives an outlet end 122a of optical fiber 118a. The optical fiber is operably interconnected at its opposite end 120a to a standard illuminator 116a.

In operation, light is directed from illuminator 116a through optical fiber 118a. This light is transmitted from outlet end 122a to depressor inlet 114a. The light is then conducted through and projected from tongue depressor 112a in a manner similar to that previously described.

Figure 7:
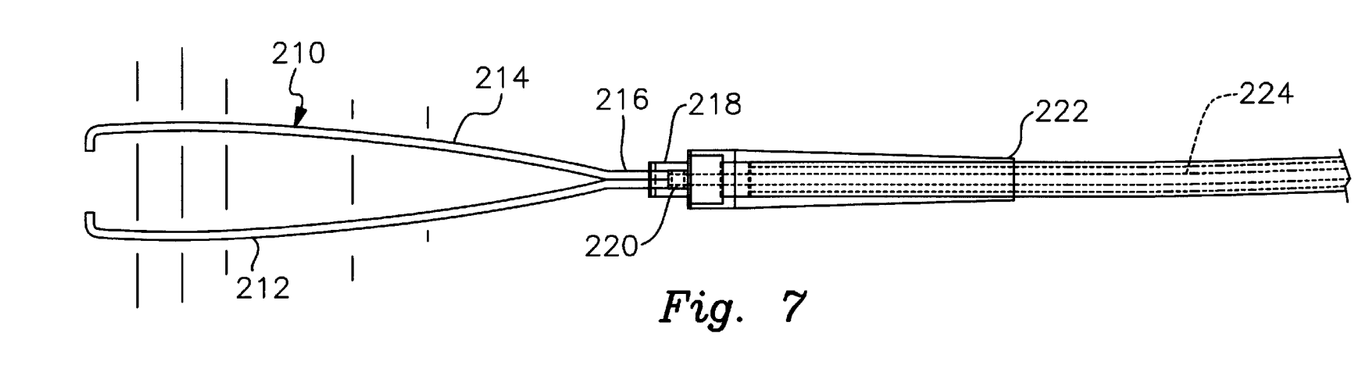
FIG. 7 is a plan view of translucent forceps according to this invention.
Figure 8:
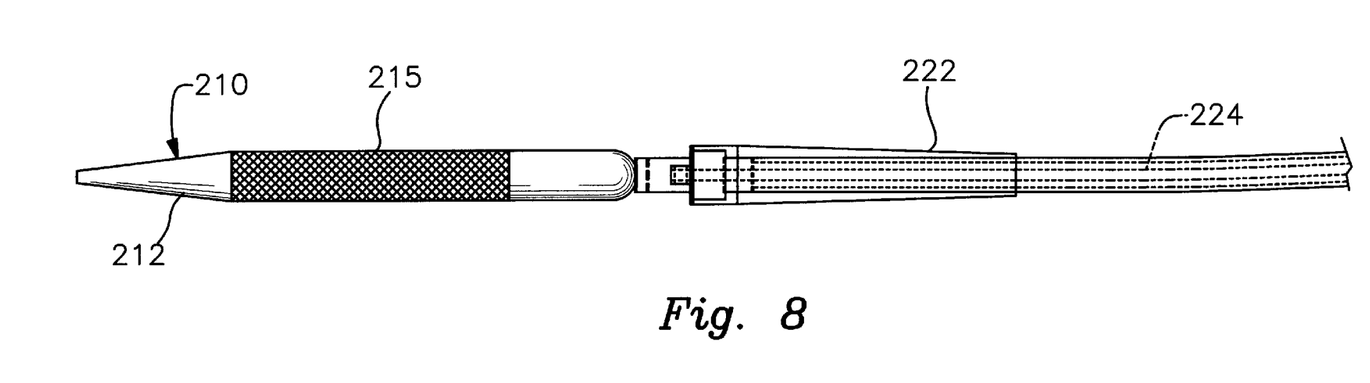
FIG. 8 is an elevational side view of the forceps of FIG. 7.

FIGS. 7 and 8 depict a pair of illuminated forceps 210. The forceps are composed of a translucent, light-conducting material. A pair of translucent grasping elements 212 and 214 merge and join at a translucent junction portion 216. The surface of these parts is entirely light emitting. The junction portion is inserted into a female fitting 218 that is communicably joined with the light-emitting end plug 220 of a standard fiberoptic cable 222. The cable 222 carries an optical fiber 224 and is connected at its opposite end to a conventional fiberoptic illuminator, not shown.

A region 215 of each of the elements 212 and 214 is knurled to facilitate handling by the physician. See FIG. 8. The forceps may be operated in a standard manner, without illumination, to grasp a particular item or body part. This will be understood as the primary function of the forceps. To illuminate the forceps, light is conducted from the illuminator through cable 222 and emitted from end plug 220 into fitting 218. Junction portion 216 transmits the light to elements 212 and 214. The junction portion and the grasping elements define a continuous, light-conducting pathway through which the light is conducted. Light is projected outwardly from the light-emitting surfaces of junction portion 216 and grasping elements 212 and 214 in the manner indicated in FIG. 7. This illuminates the area of the body being operated upon by the physician, or other item being grasped by the forceps.

Figure 9:
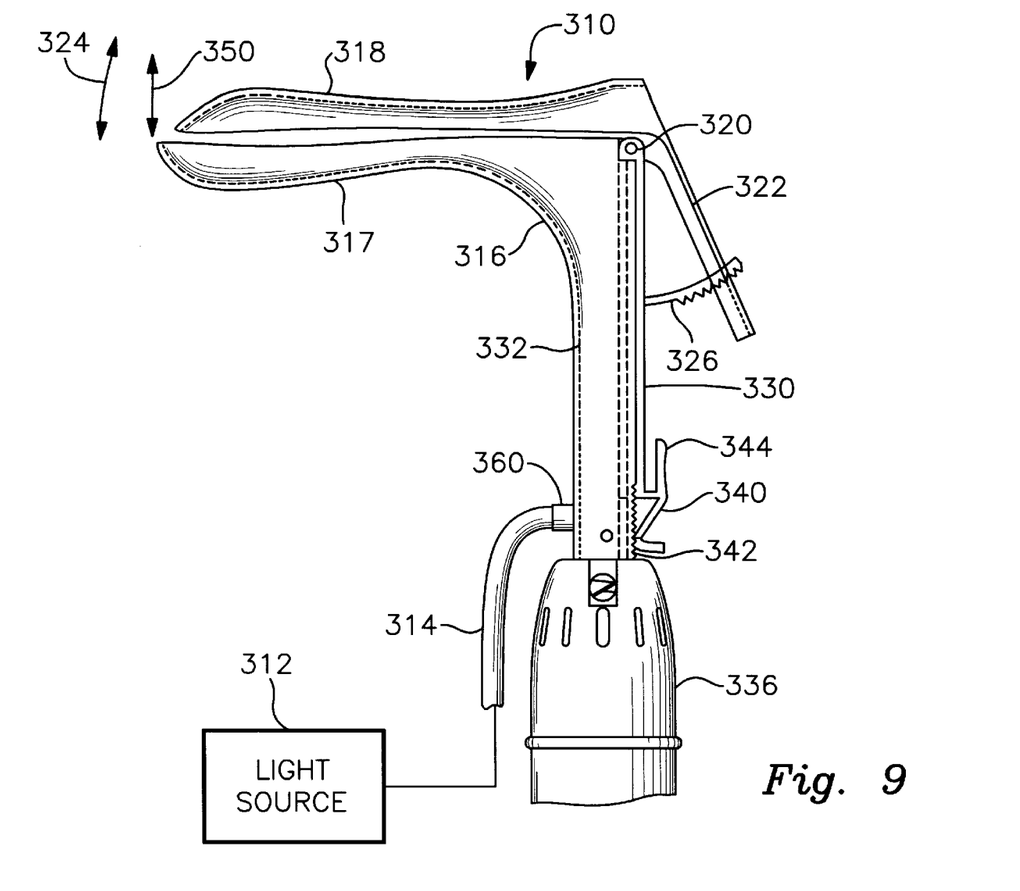
FIG. 9 is an illuminated vaginal speculum according to this invention.

A fiberoptically illuminated vaginal speculum appliance according to this invention is disclosed in FIG. 9. Appliance 310 comprises a conventional fiberoptic light source 312 and a standard fiberoptic cable 314 that is operably connected to light source 312. A translucent speculum 316 is in some regards similar in construction to conventional devices, such as the disposable, light-conductive speculum disclosed in U.S. Pat. No. 3,716,047. Specifically, speculum 316 includes a lower fixed blade 317 that is unitarily interconnected to a base 332. Base 332 is secured to a handle 336 that is held by the examining physician. Yoke 330 is slidably interengaged with a complementary slot formed in base 332. An upper blade 318 is pivotally connected to yoke 330 by a pair of pivots 320 (only one of which is shown). A pivot handle 322 permits the user to open and close blade 318, as desired, in the manner indicated by double headed arrow 324. Handle 322 includes an opening that engages a curved ratchet element 326 extending from yoke 330. The ratchet element holds handle 322 in a selected position such that blades 317 and 318 are pivoted a desired degree apart during a vaginal examination.

The lower end of yoke 330 carries a locking element 340, which is slidably engaged against a complementary ratchet element 342 mounted to base 332. A thumb tab 344 is pressed to pivot locking element 340 away from the ratchet. This permits yoke 330 to slide up and down relative to base 332, as required. By releasing thumb tab 344, locking element 340 re-engages ratchet 342 to hold yoke 330 in place. This mechanism permits the entire upper blade 318 to be raised and lowered relative to the fixed blade 317 in the manner indicated by arrow 350. Likewise, handle 322 is operated to pivot upper blade 318 relative to lower blade 317 in the manner indicated by arrow 324. The upper blade is raised and lowered or pivoted, as required, to perform a vaginal examination.

The above described structure is largely conventional and disclosed by U.S. Pat. No. 3,716,047. However, unlike that prior patent, speculum 310 does not include a light bar and does not project light across an air gap toward a predetermined focused area. Rather, in speculum 310, light is conducted through the entire body of speculum portion 316 and projected from the peripheral surface of the speculum portion. In particular, the entire operational speculum portion 316, including body 332, lower blade 317, yoke 330 and upper blade 318 comprises a translucent, light-conducting material having a light-emitting surface. A light inlet 360 is formed proximate the lower end of base 332. One end of fiberoptic cable 314 is communicably interconnected to inlet 360.

In operation, light is directed from source 312 through cable 314 to inlet 360. From there, the light is conducted through base 322 to fixed blade 317. Light is also conducted through the translucent yoke 330 to movable upper blade 318. The light is conducted through the upper and lower blades and projected from outer light-emitting surfaces 370 and 372 of those blades, respectively. See, in particular, FIG. 10. This enables the vaginal cavity to be illuminated so that a comprehensive gynecological examination can be performed.

Figure 10:
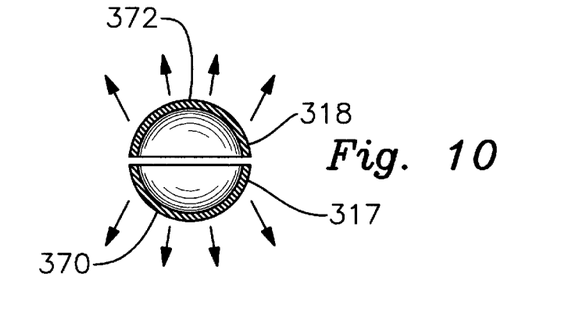
FIG. 10 is a cross sectional view of the speculum blades taken along line 10—10 of FIG. 9.

Appliance 310 represents a significant improvement over the previously known vaginal speculum disclosed in U.S. Pat. No. 3,716,047. Specifically, light is conducted through the entire operating portion of the speculum rather than through a single light-conducting bar. Light is transmitted from cable 314 through inlet 360 and from that inlet through walls 370 and 372. The light is then projected from the periphery of the speculum, as illustrated in FIG. 10, to brightly illuminate the body cavity. The light is at no time interrupted by the air while it is being conducted through the speculum 316. In the prior lighted speculum, which utilizes a light bar, light is projected from the end of the light bar toward a point proximate the end of the speculum blades. The light is thus interrupted by the air before it exits the speculum and is not conducted through and transmitted from the entire operational periphery of the appliance. As a result, optimal lighting is not achieved. Such a benefit is provided, however, by appliance 310.

Figure 11:
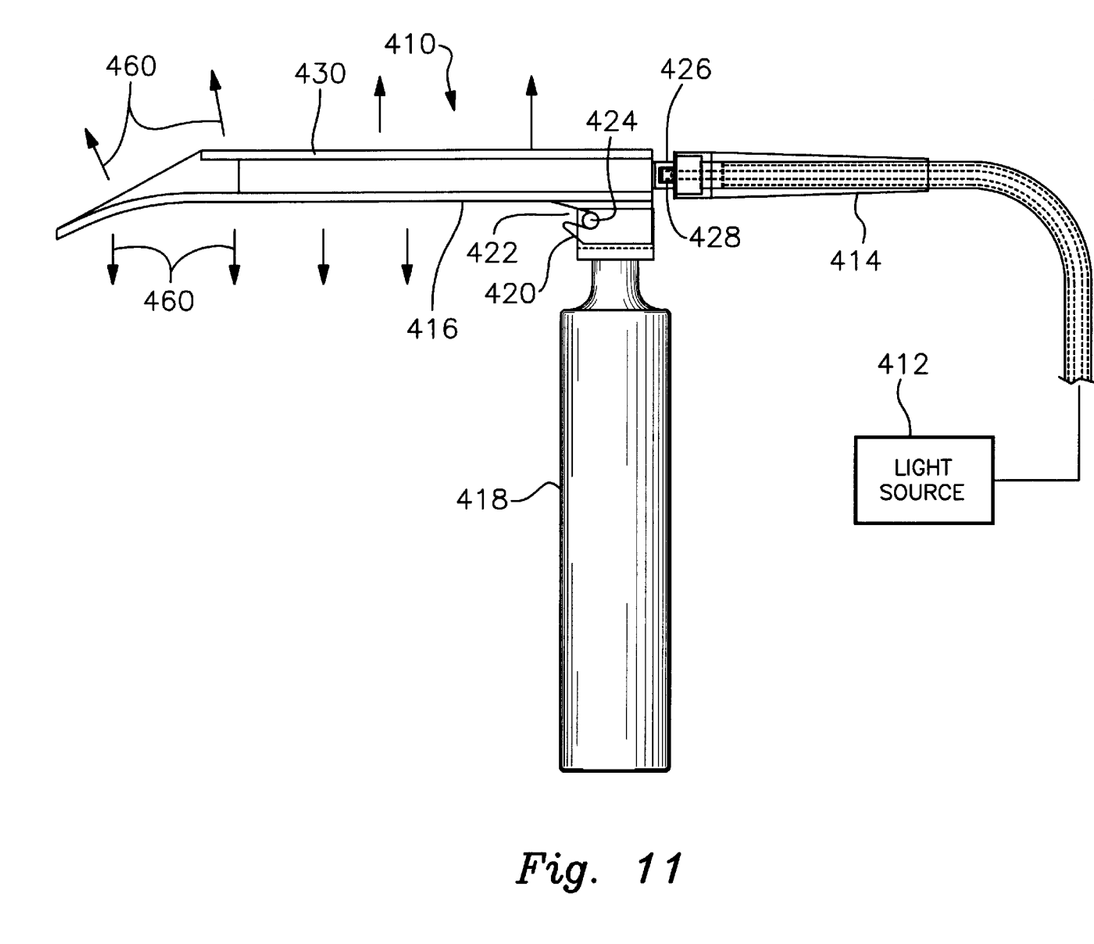
FIG. 11 is an elevational side view of a laryngoscope manufactured according to this invention.
Figure 12:
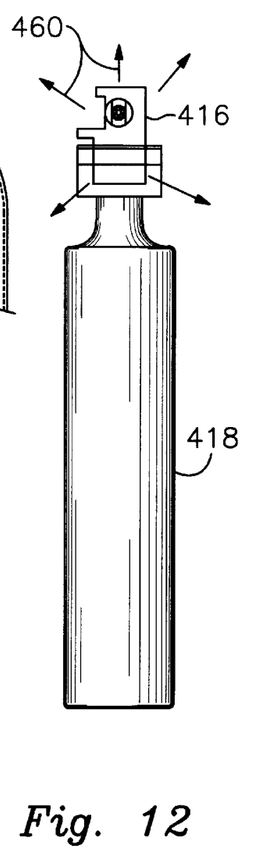
FIG. 12 is an elevational rear end of the laryngoscope of FIG. 11.

There is shown in FIGS. 11 and 12 a fiberoptically illuminated laryngoscope 410. Again, the appliance includes a light source 412 and a light-conducting fiberoptic cable 414. A translucent operational laryngoscope blade 416 having a conventional shape is pivotally mounted to a steel or aluminum handle 418. In particular, a tab 420 depends from blade 416 and includes a recess 422 that interengages a pivot post 424 mounted to the upper end of handle 418. This manner of mounting a laryngoscope blade to a handle is well known in the art and should be understood to those persons skilled in medical appliances.

The novel aspect of this device comprises the use of a translucent, light-conducting material for laryngoscope blade 416. The blade is operable in a conventional manner to perform examinations of the throat. However, in the present invention it is interconnected with fiberoptic cable 414 to more brightly illuminate such examinations. To accomplish this, blade 416 carries a fitting 426 that extends from the rearward end of blade 416. Fitting 426 includes a threaded opening or receptacle that receives a light-projecting plug 428 at the end of fiberoptic cable 414. Plug 428 is threaded or otherwise inserted into fitting 426. The fitting is translucent and conducts light to the translucent walls 430 of laryngoscope blade 416. The entire blade includes a light-emitting surface.

In operation, light is directed from source 412 through cable 414 to fitting 426. The light is then transmitted through walls 430 of blade 416. Light is projected from the peripheral light-emitting surfaces of blade 416 in the manner indicated by arrows 460. As a result, the throat is brightly illuminated so that examination is facilitated.

Figures 13, 15:
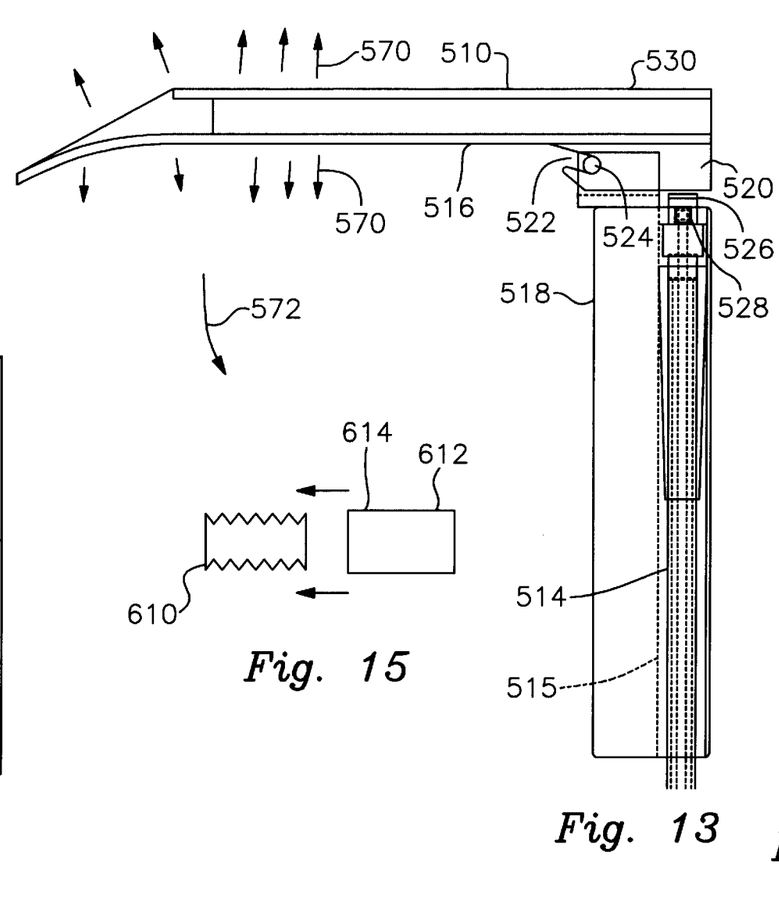
FIG. 13 is an elevational side view of an alternative translucent laryngoscope manufactured according to this invention.
FIG. 15 is a side, elevational view of a preferred connection between the appliance and the fiberoptic cable.
Figure 14:
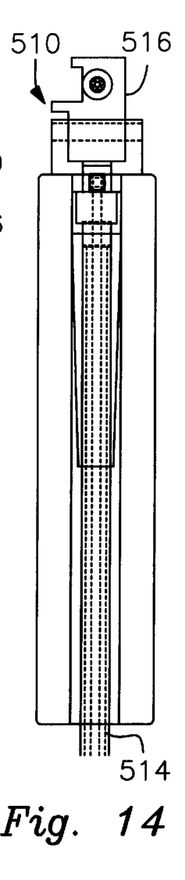
FIG. 14 is an elevational end view of the laryngoscope of FIG. 13.

An alternative illuminated laryngoscope 510 is depicted in FIGS. 13 and 14. This version employs a blade 516 that is very similar to the blade described in the previous embodiment. Indeed, blade 516 is utilized in a standard manner to perform examinations of the throat. The depending tab 520 is somewhat longer than the tab in the previously described embodiment. A light receptacle 526 is mounted below tab 520. Fiberoptic cable 514 extends through a channel 515 in handle 518. Blade 516 is again pivotally mounted to a handle 518. In particular, tab 520 includes a recess 522 that interengages a post 524 carried by handle 518.

When blade 516 is pivoted into the horizontal condition shown in FIGS. 13 and 14, receptacle 526 receives a light-emitting plug 528 carried at the end of cable 514. As a result, light is transmitted through the cable and the plug into receptacle 526. From there, the light is conducted through the translucent wall 530 of blade 510. The laryngoscope blade is again composed of a light-conducting material having a light-emitting surface. As a result, light from the fiberoptic cable is transmitted through the body 53o of blade 516 and is emitted from the blade, as indicated by arrows 570.

When laryngoscope 510 is not in use, the surgeon pivots blade 516 downwardly in the manner indicated by arrow 572. This causes receptacle 526 to disengage from light-emitting plug 528. Light ceases to be conducted through blade 516 and the blade dims.

In several of the previously described embodiments, a light-conducting receptacle is mounted to the appliance and that receptacle has been operably interengaged by a light-emitting plug or similar means. In alternative embodiments, the light appliance inlet and the fiberoptic cable may comprise the components shown in FIG. 15. For example, the appliance may carry a ribbed inlet 610 that comprises a translucent material. The distal end of the fiberoptic cable 612 may comprise a sleeve 614 that slides onto and circumferentially interengages fitting 610. It should be understood that a wide variety of other means of interengagement may also be employed.

Figure 16:
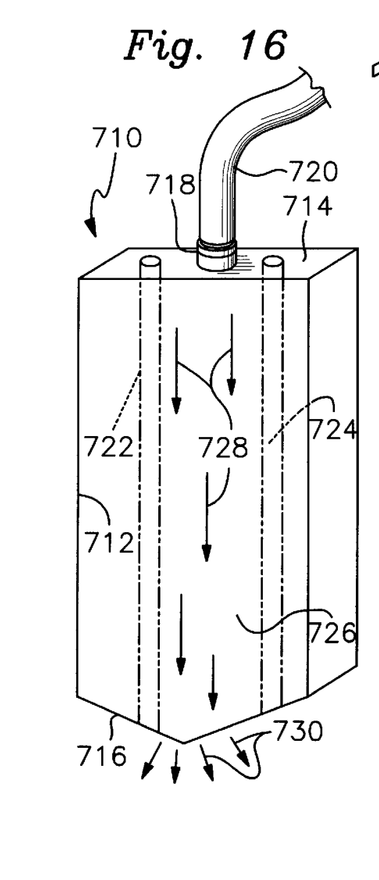
FIG. 16 is a perspective view of a translucent trocar element according to this invention.

There is shown in FIG. 16 an endoscopic trocar 710 that is fiberoptically illuminated according to this invention. Trocar 710 includes a translucent element 712 that has a generally flat upper end 714 and a sharpened or pointed lower end 716. An inlet fitting 718 is interengaged with the distal end of a fiberoptic cable 720. The opposite end of the cable, not shown, is operably interengaged with a fiberoptic light source. A pair of longitudinal channels 722 and 724 are formed in element 712 and extend from upper end 714 to lower end 716. This defines a pathway 726 between the channels.

In operation, trocar element 712 is inserted into the body through a standard trocar tube, not shown. The lower sharpened end 16 is then pressed against an organ or portion of the body being examined or otherwise operated upon. Light from the fiberoptic light source is directed through cable 720 to inlet 718. The light is transmitted longitudinally through translucent element 712 in the manner indicated by arrows 728. The pathway 726 formed by channels 722 and 724 confines the light primarily to the path indicated by arrows 728. This light is projected from the sharpened end 716 in the manner indicated by arrows 730. As a result, the blood vessels contained in the organ or other portion of the body being examined are illuminated. The surgeon can inspect these blood vessels using an appropriate means.

It should be understood that a wide variety of additional appliances may be manufactured according to this invention. These include, but are not limited to, stylets, suction tubes, catheters, endoscopic suction devices, otoscope blades, nasoscope blades, rectal tubes, sigmoidoscopes and anoscopes. In each such appliance, the body of the operational appliance itself serves to conduct light therethrough such that light is projected from the surface of the appliance onto the area being illuminated. In each case, the portion of the appliance conducting the light performs a function separate and apart from lighting. For example, in the examples described above, these functions include dental suction, tongue depression, vaginal examination, forcep operation, laryngoscopy, etc. According to this invention, light is transmitted through and projected from the operational portion of the appliance so that significantly improved illumination is achieved. These appliances are particularly effective for use in surgical, dental and medical procedures. However, they are not limited to such applications.

In each of the embodiments of this invention, operational means are featured. Such means perform a primary function (i.e. dental suction, tongue or throat examination, vaginal examination, etc.) exclusive of (e.g. other than) lighting. For example, in the embodiment of FIG. 1, the operational means comprise tubular member 18 and bulbous tip 34. Tongue depressors 112 and 112a are likewise the operational means, FIGS. 4 and 6. In FIGS. 7 and 8, the forcep elements 212, 214 and the junction portion 216 comprise the operational means. In the remaining embodiments, the operational means comprise the entire vaginal speculum 316, the laryngoscope blades 416 and 516, and the trocar 712. In each case, the operational means defines a continuous, light conducting pathway. This pathway is established by tubular wall 19, tongue depressor blade 112, the junction portion and forcep elements in the embodiments of FIGS. 7 and 8, and the laryngoscope walls 430. The trocar body also establishes a continuous light conducting pathway 725. In addition to conducting light in the above described manner each operational means is introduced into and engagable with the human body in order to perform a selected medical or surgical function unrelated to lighting (i.e. the primary function).

Although specific features of the invention are shown in some drawings and not others, this is for convenience only, as each feature may be combined with any or all of the other features in accordance with the invention. Other embodiments will occur to those skilled in the art and are within the following claims.

What is claimed is:

1. Fiberoptically illuminated forceps comprising:
   a light source;
   an elongate fiberoptic cable, which is operably interengaged to said light source and which conducts light from said light source;
   forceps including a pair of translucent, light conducting grasping elements that merge and join at a translucent junction portion, said grasping elements and said junction portion defining a continuous light-conducting pathway, and having respective light emitting outer surfaces; and
   an optical fitting that interconnects said cable and said junction portion, said optical fitting including a first opening that receives said junction portion and a second opening that receives a light emitting end plug of the cable in direct interengagement with said junction portion, whereby light is directed from said cable into said junction portion and through said continuous light-conducting pathway to said light emitting outer surfaces, from which said surfaces light is projected.

2. A fiberoptically illuminated vaginal speculum appliance comprising:
   a light source;
   an elongate fiberoptic cable, which is operably interengaged to said light source and which conducts light from said light source;
   a speculum including an elongate base, a lower blade fixedly connected to said base and extending at an angle therefrom, a yoke longitudinally slidably interengaged with said base and an upper blade pivotably connected to said yoke, said yoke being slidable relative to said base such that said upper blade is moved selectively toward and away from said lower blade, each of said base, said lower blade, said upper blade and said yoke consisting exclusively of a translucent, light-conducting material, which defines a continuous light-conducting pathway, and having respective light emitting outer surfaces; and
   means for communicably interengaging said cable and said base, said means for communicably interengaging including an optical fitting that is carried by and extends laterally outwardly from said base, said fitting being communicably interengaged by said cable, whereby light is directed from said cable through said continuous light-conducting pathway to said light emitting outer surfaces, from which said surfaces light is projected to illuminate a vaginal examination.

3. A fiberoptically illuminated trocar comprising:
   a light source;
   an elongate fiberoptic cable, which is operably interengaged to said light source and which conducts light from said light source;
   an endoscopic trocar that consists exclusively of a translucent, light-conducting element having an upper end and a convex lower end, said trocar defining a continuous light-conducting pathway, uninterrupted by air, and having a light emitting outer surface formed on a periphery thereof, said trocar including a pair of substantially parallel channels extending longitudinally therethrough from said upper end to said lower end to define a light conducting pathway between said channels; and
   an optical fitting carried by and extending upwardly from said upper end of said light conducting element, which fitting interengages said cable and said upper end of said light-conducting element and directs light from said cable into said trocar, whereby the light is transmitted through said continuous light-conducting pathway to said light emitting outer surface at said pointed lower end of said trocar, from which said surface light is projected to illuminate a medical examination employing said trocar.

\* \* \* \* \*